United States Patent [19]

Johnson

[11] Patent Number: 5,306,234

[45] Date of Patent: Apr. 26, 1994

[54] METHOD FOR CLOSING AN ATRIAL APPENDAGE

[76] Inventor: W. Dudley Johnson, N-128 W-17741 Holy Hill Rd., Germantown, Wis. 53022

[21] Appl. No.: 35,418

[22] Filed: Mar. 23, 1993

[51] Int. Cl.$^5$ .......................................... A61M 31/00
[52] U.S. Cl. ...................................... 604/49; 128/898
[58] Field of Search .................. 604/49; 128/129, 130, 128/898; 606/46

[56] References Cited

U.S. PATENT DOCUMENTS

| | | | |
|---|---|---|---|
| 4,423,730 | 1/1984 | Gabbay | 604/175 |
| 4,943,277 | 7/1990 | Bolling | 604/96 |

OTHER PUBLICATIONS

Cardiovascular Fiberoptic Endoscopy: Development and Clinical Application Tatsuzo Tanabe, M.D., et al. 1980 The C. V. Mosby Co.

Special Pacemaker Catheter Techniques The Transmediastinal placement of sensing electrodes M. Kleinert, M.D., et al.

Case Report—Thorac. cardiovasc. Surgeon 33 (1985) 128-130 Georg Thieme Verlag Stuttgart—New York.

Manometric Findings in Dysphagia Secondary to Left Atrial Dilatation Digestive Diseases and Sciences, vol. 36, No. 5 (May 1991).

Endobronchial Resection with the Nd-YAG Laser-Two Years Experience in an Australian Unit Aust NZ J Med 1990; 20 Pierce, et al.

Technical Note Mediastinoscope: Another Use J Cardiovasc Surg, 27, 1986.

Surgical Technique-Fiberoptic Examination of the Inferior Vena Cava During Circulatory Arrest for Complete Removal of Renal Cell Carcinoma Thrombus Alan R. Hartman, M.D., et al Surgery 1990; 107:695-697.

*Primary Examiner*—C. Fred Rosenbaum
*Assistant Examiner*—Michael Rafa
*Attorney, Agent, or Firm*—Foley & Lardner

[57] ABSTRACT

A method for operating on a heart is described. The method is directed to closing the passage between an atrium and its associated atrial appendage or completely removing the appendage. The method is structured to permit manipulation of the appendage without severing the sternum or ribs of the patient being operated upon. Rather, openings are made between the ribs to provide access to the heart for observation with a thoroscope and manipulation with appropriate surgical instruments.

23 Claims, 2 Drawing Sheets

METHOD FOR CLOSING AN ATRIAL APPENDAGE

FIELD OF THE INVENTION

The present invention generally relates to procedures for treating heart disease, and more particularly, relates to a method for preventing blood flow between an atrium of a heart and the associated atrial appendage.

BACKGROUND OF THE INVENTION

There are a number of heart diseases (e.g. coronary artery disease, mitral valve disease) which have various adverse effects on the heart. An adverse effect of a disease, such as mitral valve disease, is atrial (or auricular) fibrillation. During this type of fibrillation, the atria, rather than the sinus node, initiates the impulses which cause contraction of the heart muscle. In some patients, atrial fibrillation may occur in the absence of any other known disease. However, these impulses are relatively rapid and erratic, and do not properly control the contractions of the heart. As a result, the atria beat faster than the ventricles, the ventricular contractions are irregular, the ventricles do not completely fill, with blood, and the ventricular contractions eject less blood into the greater vessels.

One of the many problems caused by atrial fibrillation is the pooling of blood in the left atrial appendage during fibrillation. When blood pools in the atrial appendage, blood clots can accumulate therein, build upon themselves, and propagate out from the atrial appendage into the atrium. These blood clots can cause serious problems when the heart resumes proper operation (beating) and the blood, along with the blood clot(s), is forced out of the left atrial appendage. Similar problems also occur when a blood clot extending from an atrial appendage into an atrium breaks off and enters the blood supply. More specifically, the blood from the left atrium and ventricle supply the heart and brain. Thus, the blood flow will move the clots into the arteries of the brain and heart which may cause a obstruction in blood flow resulting in a stroke or heart attack.

One procedure which has been used to eliminate the problems caused by blood clotting in the left atrial appendage is to close (stitch off or remove) the left atrial appendage in patients which are prone to atrial fibrillation. However, this procedure presently can only be performed with the chest opened. Accordingly, since the risk of danger from stroke or heart attack due to blood clotting in the left atrial appendage are relatively low when compared to the problems and trauma involved in opening the chest; the chest is almost never opened for the sole purpose of closing or removing the left atrial appendage.

Thus, it would be useful to provide for a method of removing or closing an atrial appendage without the need to open the chest cavity.

SUMMARY OF THE INVENTION

The present invention provides a method for eliminating blood flow between an atrium of a heart and an atrial appendaqe coupled to the heart. This method may include sewing the passage between the atrium and atrial appendage closed, or removing the atrial appendage. Either of these steps is performed without opening the chest of the patient. This is accomplished by utilizing a device or group of devices which permit observation of the heart and manipulating of heart tissue from the exterior of a chest cavity which has its sternum and ribs maintained intact at the time the atrial appendage is manipulated. In other words, the method of the present invention is accomplished without bisecting the chest as is done during open-heart surgery.

BRIEF DESCRIPTION OF THE DRAWINGS

The preferred embodiment of the invention will hereafter be described with reference to the accompanying drawings, wherein like numerals denote like elements, and.

DETAILED DESCRIPTION OF THE PREFERRED EMBODIMENT

Figure 1:
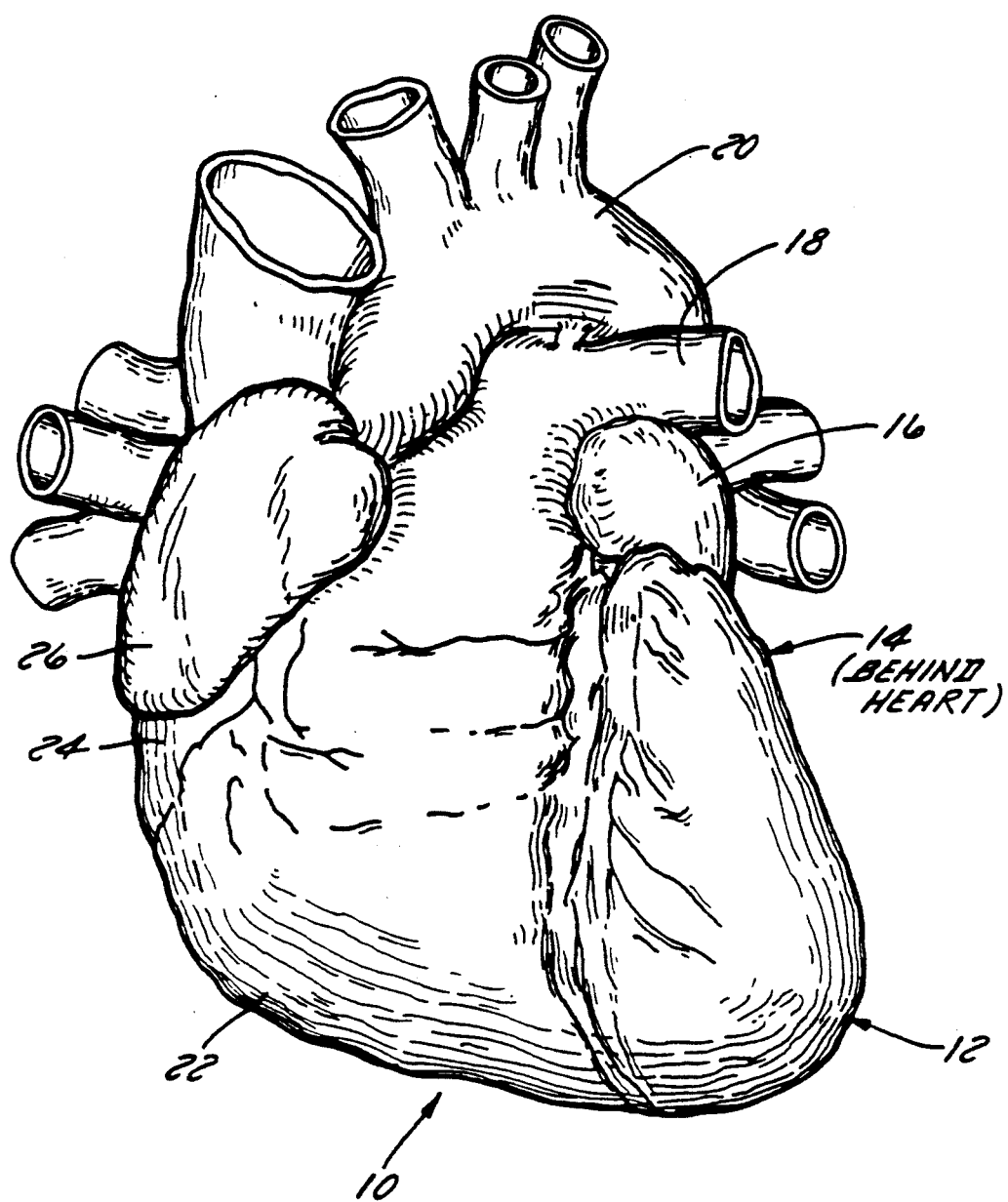
FIG. 1 is an anterior view of a heart and the proximal parts of the great vessels.
Figure 2:
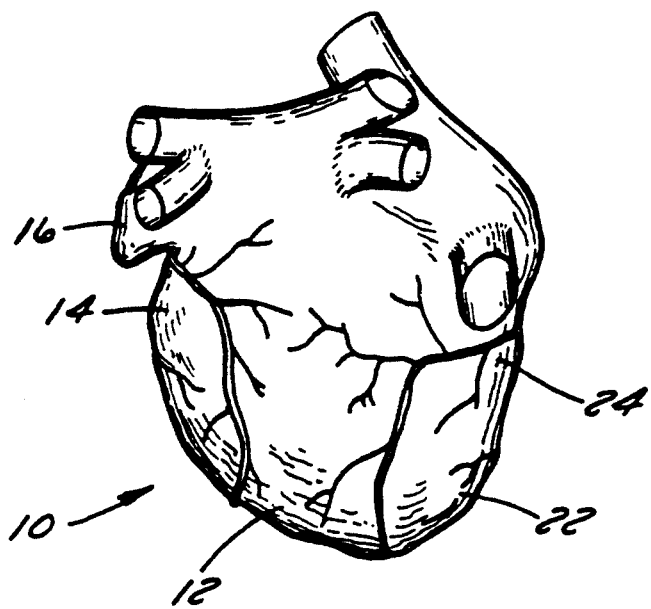
FIG. 2 is a schematic representation of the heart as viewed from its posterior side.

Referring to FIG. 1, a heart 10 is illustrated to show certain portions of the heart including the left ventricle 12, the left atrium 14, the left atrial appendage 16, the pulmonary artery 18, the aorta 20, the right ventricle 22, the right atria 24, and the right atrial appendage 26. Of particular interest are the left ventricle 12, left atrium 14 and left atrial appendage 16. As is well known, the left atrium 14 is located above left ventricle 12 and the two are separated by the mitral valve. Left atrial appendage 16 is normally in fluid communication with left atrium 14 such that blood flows in and out of the appendage 16 as heart 10 beats. FIG. 2 generally illustrates the above-discussed parts of heart 10 from the posterior surface. As discussed above, the present invention relates to a method for closing the passage between an atrium and an associated atrial appendage, or completely removing the appendage. The present embodiment provides a method for closing the passage between left atrium 14 and left atrial appendage 16 to eliminate the problems caused by blood clotting in appendage 16 during fibrillation.

Figure 3:
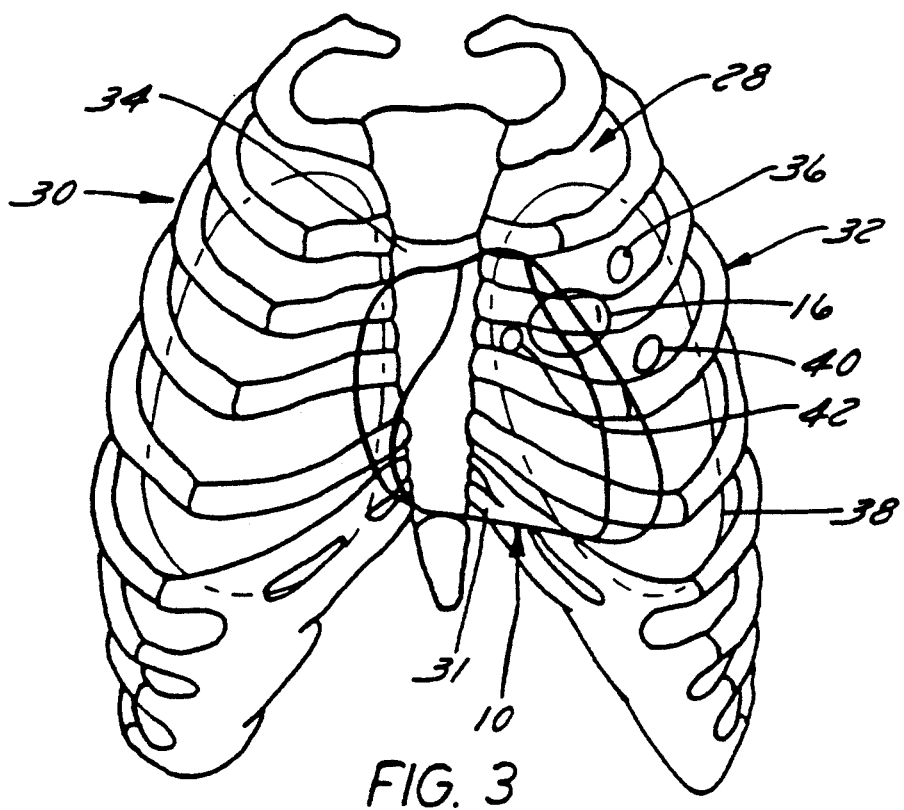
FIG. 3 is a schematic representation of the heart and associated chest cavity.

Referring to FIG. 3, a chest cavity 28 is shown which is defined by a plurality of right ribs 30 and left ribs 32 which are supported relative to each other by a sternum 34. The position of heart 10 is generally represented in reference to the chest cavity by a line labeled with the reference numeral 10. The position of atrial appendage 16 is generally represented by the circle marked 16.

The method of closing the passage to atrial appendage 16 will now be discussed in detail. The first step of the preferred method is to determine the number and location of openings which will be made into chest cavity 28. The position of the openings is between ribs 32, and generally in the vicinity of appendage 16. The number of openings will depend upon the specific instruments used and preference of the surgeon. However, as discussed below, the presently contemplated number of openings is three (3).

The second step is to open or administer an appropriate general anesthetic to the patient and make a first opening between selected ribs 32 into chest cavity 28. Subsequently, the left lung is collapsed using a double lumen endotracheal tube in combination with the introduction of carbon dioxide into cavity 10 through the first opening to collapse the left lung.

The third step is to open or remove a portion of the pericardium so that access to left atrial appendage 16 is provided. Preferably, this step involves providing one or two more openings between selected ribs 32 into chest cavity 28 and possibly removing the carbon dioxide source from the first opening. Subsequently, a device which permits observation of the interior of cavity 28 by a surgeon (e.g. thoroscope which permits observation of the interior of cavity 10 from the exterior) is introduced into one of the openings and a device which permits manipulation of the heart tissue for purposes of cutting the tissue (e.g. knife with appropriate extension or operating mechanism to permit cutting of tissue within cavity 10 from the exterior of cavity 10) is introduced through another of the openings. With the thoroscope and knife in position, a portion of the pericardium is removed to provide access to the left atrial appendage 16.

In one embodiment, the thoroscope may include fiber optics properly coupled to a camera to produce a view of the surgical site on a video monitor (t.v. screen).

By way of modification, a laser suitable for operating purposes could be used in place of, or in conjunction with the knife. Where the laser is used in conjunction with the knife, a device for directing the energy of the laser (fiberoptic) is inserted into cavity 28 through the third opening. One advantage of using a laser is the ability to better control bleeding while using the laser for purposes of cutting heart and surrounding tissue. Various lasers could be used, such as, but not necessarily restricted to, HO:YAG, KTP and Nd:YAG.

The fourth step is to replace either the knife or laser with a tissue joining device (e.g. a suturing or stapling device which is manipulated by a surgeon from the exterior of cavity 28 to accomplish suturing or stapling within the cavity) which is extended into cavity 10. With the joining device extending into cavity 10, the surgeon can suture (sew) or staple the passage between left atrium 14 and left atrial appendage 16 closed. Thus, the appendage may be left as an occluded blind pouch. Subsequently, depending upon the situation, appendage 16 may be severed from the heart using the knife or laser, and removed from the chest cavity 28.

Subsequent to providing access to heart 10, and before closing the passage between appendage 16 and atrium 14, it may be necessary to determine if a clot is present at the location of closure. By making this determination, it may be possible to avoid causing a clot or portion of a clot to enter the blood stream by reducing the risk of disturbing a clot during the closing procedure. By way of example the step of determining the presence of a clot may be carried out with a probe including a transducer, such as an ultrasonic probe, which is positioned at the base of appendage 16 to determine if a clot is present at the selected location for sutures or staples.

An important step of the above-described method is that access to heart 10 is made through openings into cavity 28 which pass between ribs. This step allows the surgeon to maintain the sternum and ribs intact during the operation to close or remove appendage 16. More generally stated, the present method permits operating upon the heart (removal of appendage 16) without bisecting the patient. Additionally, the present method would be performed while the heart is beating.

It will be understood that the foregoing description of the preferred exemplary embodiment of the inventive method does not limit the method to particular instruments or details of the procedural step. For example, depending upon the patient and circumstances, the surgeon may use one or more combinations of the following list of instruments: Auto Suture and Surgiport devices manufactured by United States Surgical Corp.; a lung holder (forceps) manufactured by Ethicon; and an Endopath Automatic Stapler manufactured by Ethicon. Rather, the method is designed to permit physiologic severing of heart tissue without the need to bisect the patient. Accordingly, other modifications may be made to the disclosed method without departing from the scope of the invention and expressed in the appended claims.

What is claimed is:

1. A method for manipulating tissue of the heart, where the heart is located within a chest cavity defined by a sternum and an associated set of ribs and the heart includes an atrium and atrial appendage having a fluid passage therebetween, the method comprising the steps of:
 a) inserting an observation device into the chest cavity to permit observation of heart tissue from the exterior of the chest cavity, where the device is inserted at a first position between two ribs;
 b) inserting a manipulation device into the chest cavity to permit operation on heart tissue from the exterior of the chest cavity, where the device is inserted at a second position between two ribs;
 c) positioning the manipulation device substantially proximate a selected tissue area of the heart and operating on the selected tissue; and
 d) maintaining the sternum and ribs intact during the execution of steps a–c.

2. The method of claim 1, where the selected tissue is the atrial appendage, and the method further comprise the step of removing the appendage from the heart.

3. The method of claim 1, where the selected tissue is an atrial appendage, and the method further comprise the steps of sewing the appendage at the passage with its associated atrium to prevent blood flow therebetween.

4. The method of claim 1, where the selected tissue is an atrial appendage, and the method further comprises the step of stapling the appendage at the passage to prevent blood flow therebetween.

5. The method of claim 1, further comprising the step of removing a portion of a pericardium associated with the heart.

6. The method of claim 3, further comprising the step of determining if a blood clot is present at the passage.

7. The method of claim 4, further comprising the step of determining if a clot is present at the passage.

8. A method for eliminating a passage for blood flow located between the left atrium of a heart and the left atrial appendage, where the heart is located within a chest cavity defined by a sternum and an associated set of ribs, the method comprising the steps of:
 a) inserting an observation device into the chest cavity to permit observation of heart tissue from the exterior of the chest cavity, where the device is inserted at a first position between two ribs;
 b) inserting a manipulation device into the chest cavity to permit manipulation of heart tissue from the exterior of the chest cavity, where the device is inserted at a second position between two rib;
 c) positioning the manipulation device substantially proximate the passage for blood flow located between the left atrium and the left atrial appendage;
 d) manipulating the atrial appendage such that the passage for blood flow is closed; and e) maintaining the sternum and ribs intact during the execution of steps a-d.

9. The method of claim 8, further comprising the step of removing the atrial appendage.

10. The method of claim 9, further comprising the step of inserting a device for directing laser energy into the chest cavity where the atrial appendage is removed.

11. The method of claim 8, where the step of manipulating the atrial appendage includes sewing shut the passage for blood flow.

12. The method of claim 8, where the step of manipulating the atrial appendage includes the step of stapling shut the passage for blood flow.

13. The method of claim 8, further comprising the step of removing a portion of a pericardium associated with the heart.

14. The method of claim 11, further comprising the step positioning a probe to determine if a clot is present at the location of blood flow.

15. The method of claim 12, further comprising the step positioning a probe to determine if a clot is present at the location of blood flow.

16. A method for eliminating a passage for blood flow located between the left atrium of a heart and the left atrial appendage, where the heart is located within a chest cavity of a patient, where the cavity is defined by a sternum and an associated set of ribs, the method comprising the steps of:
   a) applying a general anesthetic to the patient;
   b) collapsing the left lung of the patient;
   c) making a first opening into the chest cavity at a first location between two ribs;
   d) extending a thoroscope into the first opening and orienting the thoroscope in a position to observe the left atrial appendage and surrounding heart tissue;
   e) making a second opening into the chest cavity at a second location between two ribs;
   f) inserting a manipulation device into the second opening to permit manipulation of heart tissue from the exterior of the chest cavity;
   g) positioning the manipulation device substantially proximate the passage for blood flow located between the left atrium and the left atrial appendage;
   h) manipulating the atrial appendage such that the passage for blood flow is closed; and
   i) maintaining the sternum and ribs intact during the execution of steps a-h.

17. The method of claim 16, where the step of manipulating the atrial appendage includes removing the appendage.

18. The method of claim 17, further comprising the step of inserting a device for directing laser energy into the chest cavity to bleeding.

19. The method of claim 16, where the step of manipulating the atrial appendage includes sewing shut the passage for blood flow.

20. The method of claim 16, where the step of manipulating the atrial appendage includes stapling shut the passage for blood flow.

21. The method of claim 16, further comprising the step of removing a portion of a pericardium associated with the heart.

22. The method of claim 19, further comprising the step positioning a probe to determine if a clot is present at the location of blood flow.

23. The method of claim 20, further comprising the step positioning a problem to determine if a clot is present at the location of blood flow.

* * * * *

UNITED STATES PATENT AND TRADEMARK OFFICE
CERTIFICATE OF CORRECTION

PATENT NO. : 5,306,234
DATED : April 26, 1994
INVENTOR(S) : W. Dudley Johnson

It is certified that error appears in the above-identified patent and that said Letters Patent is hereby corrected as shown below:

Col. 2, line 48, change "10" to --31--;
Col. 2, line 62, after "opening" insert --36--;
Col. 2, line 63, after "lung" insert --38--;
Col. 2, line 65, change "10" to --28--;
Col. 2, line 66, after "opening" insert --36--;
Col. 2, line 66, after "lung" insert --38--;
Col. 3, line 2, after "openings" insert --40 and 42--;
Col. 3, line 7, change "10" to --28--;
Col. 3, line 12, change "10" to --28--;
Col. 3, line 34, change "10" to --28--;
Col. 3, line 35, change "10" to --28--; and
Col. 3, line 57, after "ribs" insert --32--.

Signed and Sealed this

Fifteenth Day of August, 2000

Attest:

Q. TODD DICKINSON

*Attesting Officer*     *Director of Patents and Trademarks*